(12) United States Patent
Ishii et al.

(10) Patent No.: US 6,506,943 B1
(45) Date of Patent: Jan. 14, 2003

(54) PROCESS FOR PRODUCING ALDEHYDES

(75) Inventors: Yasutaka Ishii, Takatsuki (JP); Tatsuya Nakano, Himeji (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/700,021

(22) PCT Filed: Feb. 22, 2000

(86) PCT No.: PCT/JP00/00987

§ 371 (c)(1),
(2), (4) Date: Jan. 12, 2001

(87) PCT Pub. No.: WO00/53554

PCT Pub. Date: Sep. 14, 2000

(30) Foreign Application Priority Data

Mar. 9, 1999 (JP) ............................................. 11-062444

(51) Int. Cl.[7] ......................... C07C 45/32; C07C 47/02; C07C 47/54; C07C 47/04; B01J 31/24
(52) U.S. Cl. ......................................... 568/431; 568/47
(58) Field of Search ................................. 568/431, 471

(56) References Cited

U.S. PATENT DOCUMENTS

| 3,991,117 A | 11/1976 | Zeidler et al. ........ 260/603 HF |
| 5,274,187 A | * 12/1993 | Kimura et al. .............. 562/538 |

FOREIGN PATENT DOCUMENTS

| FR | 2460908 | 1/1981 |
| GB | A2312209 | 10/1997 |
| JP | A55102528 | 8/1980 |
| JP | A57192326 | 11/1982 |
| JP | A11226417 | 8/1999 |

OTHER PUBLICATIONS

Tomioka et al., Tetrahedron Letters, vol. 22, No. 17, 1981, pp. 1605–1608.*
T.W. Graham Solomons, Organic Chemistry, fourth edition, 1976, p. 713.*
Takezawa et al., Org. Lett., 1999, vol. 1(5), pp. 713–715.*
Coleman et al., Eur. J. Inorg. Chem., vol. 11, pp. 1673–1675 (1998).
Lenz et al., J. Chem. Soc., Perkin Trans., vol. 2, No. 2, pp. 3291–3292 (1997).
Marko et al., J. Am. Chem. Soc., vol. 119, No. 51, pp. 12661–12662 (1997).

* cited by examiner

Primary Examiner—Rosalynd Keys
(74) Attorney, Agent, or Firm—Birch, Stewart, Kolasch & Birch, LLP

(57) ABSTRACT

A process for producing an aldehyde of the invention allows a 1,2-diol (vic-diol) to react with oxygen in the presence of a ruthenium catalyst supported on a carrier to oxidatively cleave a bond between two carbon atoms, where hydroxyl groups are combined with the carbon atoms, to thereby yield a corresponding aldehyde. The carrier includes, for example, an activated carbon. As a catalytic component to be supported on the carrier, dichlorotris(triphenylphosphine)ruthenium(II), and other organic ruthenium complexes, for example, can be used. The invention can efficiently produce a corresponding aldehyde by oxidative cleavage of a 1,2-diol with oxygen.

3 Claims, No Drawings

PROCESS FOR PRODUCING ALDEHYDES

This application is the national phase under 35 U.S.C. § 371 of PCT International Application No. PCT/JP00/00987 which has an International filing date of Feb. 22, 2000, which designated the United States of America.

TECHNICAL FIELD

The present invention relates to a process for producing an aldehyde. Specifically, the present invention relates to a process for producing a corresponding aldehyde by oxidative cleavage of a 1,2-diol (vic-diol).

BACKGROUND ART

Processes using periodic acid or lead tetraacetate are known as processes for forming a corresponding aldehyde by oxidative cleavage of a 1,2-diol. However, the process using periodic acid can be applied only to a narrow range, as the oxidizing agent is insoluble in an organic solvent. In addition, the above processes require large amounts of compounds containing iodine or lead, and require a complicated aftertreatment and are not desirable from viewpoints of resources and environmental issues.

On the other hand, catalytic oxidation processes using oxygen as an oxidizing agent are employed as processes for oxidizing substrates without using large amounts of halogen compounds or metallic compounds. However, there are few processes for efficiently obtaining a corresponding aldehyde by oxidative cleavage of a 1,2-diol with oxygen.

DISCLOSURE OF INVENTION

Accordingly, it is an object of the present invention to provide a process for efficiently obtaining a corresponding aldehyde by oxidative cleavage of a 1,2-diol with oxygen.

After intensive investigations to achieve the above object, the present inventors found that the use of a catalyst including a ruthenium compound supported on a carrier can yield a corresponding aldehyde by oxidative cleavage of a 1,2-diol. The present invention has been accomplished on the basis of these findings.

Specifically, the present invention provides a process for producing an aldehyde. The process includes the step of allowing a 1,2-diol to react with oxygen in the presence of a ruthenium catalyst supported on a carrier to oxidatively cleave a bond between two carbon atoms, where hydroxyl groups are combined with the carbon atoms, to thereby yield a corresponding aldehyde. The carrier includes, for example, an activated carbon. An organic ruthenium complex or the like can be used as a catalytic component to be supported on an activated carbon.

BEST MODE FOR CARRYING OUT THE INVENTION

[Ruthenium Catalyst Supported on a Carrier]

The ruthenium catalyst supported on a carrier is not specifically limited as far as it is a catalyst including a ruthenium compound supported on a carrier. The term "ruthenium compound" as used in the present description also includes elementary ruthenium. The ruthenium compound includes, but is not limited to, metallic ruthenium, ruthenium oxide, ruthenium sulfide, ruthenium hydroxide, ruthenium fluoride, ruthenium chloride, ruthenium bromide, ruthenium iodide, ruthenium sulfate, ruthenic acid or salts thereof (e.g., ammonium ruthenate), perruthenic acid or salts thereof (e.g., tetrapropylammonium perruthenate), inorganic ruthenium complexes [e.g., ruthenium hydroxyhalides (e.g., ruthenium hydroxychloride), hexaammineruthenium halides (e.g., hexaammineruthenium chloride), nitrosylruthenium, hexahaloruthenic acids or salts thereof (e.g., sodium hexachlororuthenate)], and other inorganic compounds; ruthenium cyanide, organic ruthenium complexes [e.g., dodecacarbonyltriruthenium(0), dicarbonyltris(triphenylphosphine)ruthenium(II), diacetatodicarbonylbis(triphenylphosphine)ruthenium(II), dichlorotris(triphenylphosphine)ruthenium(II), dihydridotetrakis(triphenylphosphine)ruthenium(II), dichlorobis(acetonitrile)bis(triphenylphosphine)ruthenium(II), ruthenocene, and other organic compounds.

The ruthenium may have any valency of 0 to 8. The valency of ruthenium is preferably from 0 to 4, of which a valency of 2 is typically preferably.

Preferred ruthenium compounds include metallic ruthenium, perruthenic acid or salts thereof, and ruthenium complexes. Among them, metallic ruthenium and ruthenium complexes are typically preferred, of which organic ruthenium complexes, especially organic ruthenium complexes each having a phosphine such as triphenylphosphine as a ligand [e.g., dichlorotris(triphenylphosphine)ruthenium(II)] are specifically preferred. Each of these ruthenium compounds can be used alone or in combination.

The carrier includes conventional carriers for supporting catalysts, such as silica, alumina, silica-alumina, zeolite, titania, magnesia, and other inorganic metal oxides, as well as activated carbon. Among them, activated carbon is preferred from viewpoint of catalytic activity. Activated carbons obtained from a variety of materials (e.g., vegetable, mineral, or resinous materials) can be used as the activated carbon. The activated carbon may be any of gas-activated carbon or chemically activated carbon. The carrier has a specific surface area of, for example, about 10 to 3000 $m^2/g$, and preferably about 50 to 3000 $m^2/g$.

The amount of the ruthenium compound to be supported is, for example, about 0.1 to 50% by weight, preferably about 1 to 20% by weight, and more preferably about 2 to 10% by weight, relative to the weight of the carrier. The catalyst can be prepared by a conventional technique such as impregnation, precipitation, or ion exchange.

The amount of the ruthenium catalyst supported on a carrier is, for example, about 0.001 to 1 mole, preferably about 0.01 to 0.6 mole, and more preferably about 0.02 to 0.4 mole in terms of a ruthenium compound per 1 mole of the substrate 1,2-diol.

In the present invention, a base can be used as a promoter (co-catalyst). The concurrent use of a base may improve a reaction rate or a reaction selectivity in some cases. Particularly, the use of a base can remarkably enhance the reaction rate upon oxidation of a cyclic 1,2-diol. Such bases include, for example, hydroxides, carbonates, and hydrogencarbonates of alkali metals (e.g., sodium and potassium), hydroxides and carbonates of alkaline earth metals (e.g., magnesium and calcium), and other inorganic bases; triethylamine, piperidine, N-methylpiperidine, N-methylpyrrolidine, N,N-dimethylaniline, and other amines, pyridine, quinoiine, and other aromatic nitrogen-containing heterocyclic compounds, and other organic bases. Preferred bases include, carbonates and hydrogencarbonates of alkali metals, and carbonates of alkaline earth metals, of which potassium carbonate, and other carbonates of alkali metals are specifically preferred.

The amount of the base is, for example, about 0.001 to 1 mole, preferably about 0.005 to 0.2 mole, and more preferably about 0.01 to 0.1 mole, per 1 mole of the substrate 1,2-diol.

[1,2-Diol]

The 1,2-diol (vic-diol) for use as a reactant (substrate) includes terminal vic-diols, chain internal vic-diols, and cyclic vic-diols. Such 1,2-diols include, but are not limited to, a compound represented by the following formula (1):

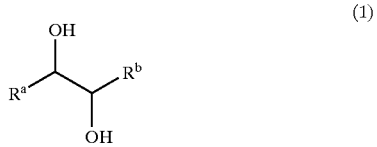

(1)

(wherein each of $R^a$ and $R^b$ is, identical to or different from each other, a hydrogen atom, a hydrocarbon group, or a heterocyclic group, where $R^a$ and $R^b$ may be combined to form a ring with adjacent two carbon atoms).

In the formula (1), the hydrocarbon group in $R^a$ and $R^b$ includes aliphatic hydrocarbon groups, alicyclic hydrocarbon groups, aromatic hydrocarbon groups, and groups each including these groups combined with each other. Such aliphatic hydrocarbon groups include, but are not limited to, methyl, ethyl, propyl, isopropyl, butyl, isobutyl, s-butyl, t-butyl, pentyl, hexyl, decyl, docecyl, and other alkyl groups each having about 1 to 20 (preferably 1 to 10) carbon atoms; vinyl, allyl, 1-butenyi, and other alkenyl groups each having about 2 to 20 (preferably 2 to 10) carbon atoms; ethynyl, propynyl, and other alkynyl groups each having about 2 to 20 (preferably 2 to 10) carbon atoms.

The alicyclic hydrocarbon groups include, but are not limited to, cyclopropyl, cyclobutyl, cyclopentyl, cyclohexyl, cyclooctyl, and other cycloalkyl groups each having about 3 to 20 members (preferably 3 to 15 members, and more preferably 5 to 8 members); cyclopentenyl, cyclohexenyl, and other cycloalkenyl groups each having about 3 to 20 members (preferably 3 to 15 members, and more preferably 5 to 8 members) The aromatic hydrocarbon groups include, for example, phenyl, naphthyl, and other aromatic hydrocarbon groups each having about 6 to 14 (preferably 6 to 10) carbon atoms.

Hydrocarbon groups each containing an aliphatic hydrocarbon group and an alicyclic hydrocarbon group combined with each other include, for example, cyclopentylmethyl, cyclohexylmethyl, 2-cyclohexylethyl, and other cycloalkyl-alkyl groups (e.g., $C_3$–$C_{20}$ cycloalkyl-$C_1$–$C_4$ alkyl groups). Hydrocarbon groups each containing an aliphatic hydrocarbon group and an aromatic hydrocarbon group combined with each other include, for example, aralkyl groups (e.g., $C_7$–$C_{18}$ aralkyl groups), and alkyl-substituted aryl groups (e.g., phenyl group or naphthyl group on which one to four $C_1$–$C_4$ alkyl groups are substituted).

Preferred hydrocarbon groups include, for example, $C_1$–$C_{10}$ alkyl groups, $C_2$–$C_{10}$ alkenyl groups, $C_2$–$C_{10}$ alkynyl groups, $C_3$–$C_{15}$ cycloalkyl groups, $C_6$–$C_{10}$ aromatic hydrocarbon groups, $C_3$–$C_{15}$ cycloalkyl-$C_1$–$C_4$ alkyl groups, and $C_7$–$C_{14}$ aralkyl groups.

The hydrocarbon group may have a variety of substituents such as halogen atoms, oxo group, hydroxyl group, substituted oxy groups (e.g., alkoxy groups, aryloxy groups, aralkyloxy group, and acyloxy groups), carboxyl group, substituted oxycarbonyl groups, substituted or unsubstituted carbamoyl groups, cyanogroup, nitrogroup, substitutedorunsubstituted amino groups, and heterocyclic groups.

Heterocyclic rings for constituting the heterocyclic group in $R^a$ and $R^b$ include aromatic heterocyclic rings and non-aromatic heterocyclic rings. Such heterocyclic rings include, but are not limited to, heterocyclic rings each containing an oxygen atom as a heteroatom (e.g., furan, tetrahydrofuran, oxazole, isoxazole, and other 5-membered rings, 4-oxo-4H-pyran, tetrahydropyran, morpholine, and other 6-membered rings, benzofuran, isobenzofuran, 4-oxo-4H-chromene, chroman, isochroman, and other condensed rings), heterocyclic rings each containing a sulfur atom as a heteroatom (e.g., thiophene, thiazole, isothiazole, thiadiazole, and other 5-membered rings, 4-oxo-4H-thiopyran, and other 6-membered rings, benzothiophene and other condensed rings), heterocyclic rings each containing a nitrogen atom as aheteroatom (e.g., pyrrole, pyrrolidine, pyrazole, imidazole, triazole, and other 5-membered rings, pyridine, pyridazine, pyrimidine, pyrazine, piperidine, piperazine, and other 6-membered rings, indole, indoline, quinoline, acridine, naphthyridine, quinazoline, purine, and other condensed rings). These heterocyclic groups may have substituents. Such substituents include, for example, the substituents which the hydrocarbon groups may have, as well as alkyl groups (e.g., methyl, ethyl, and other $C_1$–$C_4$ alkyl groups), cycloalkyl groups, and aryl groups (e.g., phenyl and naphthyl groups).

The substituents $R^a$ and $R^b$ may be combined to form a ring with adjacent two carbon atoms. Such rings include, but are not limited to, cyclobutane, cyclopentane, cyclohexane, cyclohexene, cyclooctane, cyclododecane, and other non-aromatic carbon rings (cycloalkane rings or cycloalkene rings) each having about 3 to 20 members (preferably 3 to 15 members, and more preferably 5 to 12 members); oxolane, oxane, azolidine, perhydroazine, thiolane, thiane, and other non-aromatic heterocyclic rings (especially, non-aromatic heterocyclic rings each containing an oxygen atom, a nitrogen atom, or a sulfur atom) each having about 3 to 20 members (preferably 3 to 12 members, and more preferably 3 to 8 members). These rings may have any of the substituents, and other rings (non-aromatic or aromatic rings) may be condensed to these rings.

Preferred $R^a$ and $R^b$ include hydrogen atom, $C_1$–$C_{10}$ alkyl groups, $C_2$–$C_{10}$ alkenyl groups, $C_2$–$C_{10}$ alkynyl groups, $C_3$–$C_{15}$ cycloalkyl groups, $C_6$–$C_{10}$ aromatic hydrocarbon groups, $C_3$–$C_{12}$ cycloalkyl-$C_1$–$C_4$ alkyl groups, and $C_7$–$C_{14}$ aralkyl groups. Alternatively, $R^a$ and $R^b$ are preferably combined to form, with adjacent two carbon atoms, a non-aromatic carbon ring or non-aromatic heterocyclic ring having about 3 to 20 members.

Typical examples of the 1,2-diols represented by the formula (1) include, but are not limited to, ethylene glycol, 1,2-propanediol, 1,2-butanediol, 2,3-butanediol, 1,2-pentanediol, 2,3-pentanediol, 1,2-hexanediol, 2,3-hexanediol, 3,4-hexanediol, 1,2-heptanediol, 1,2-octanediol, 2,3-octanediol, 3,4-octanediol, 1,2-nonanediol, 1,2-decanediol, 1-phenyl-1,2-ethanediol, 3-phenyl-1,2-propanediol, 1-(2-pyridyl)-1,2-ethanediol, 1-cyclohexyl-1,2-ethanediol, polyhydric alcohols (e.g., xylitol, sorbitol, mannitol, and other alditols, or derivatives thereof), and other chain 1,2-diols; 1,2-cyclopentanediol, 1,2-cyclohexanediol, 1,2-cyclooctanediol, cyclitols (e.g., inositcl or derivatives thereof), saccharides (e.g., ribose, xylose, glucose, mannose, fructose, cellulose, starch, amino sugars, or derivatives thereof), and other cyclic 1,2-diols.

[Oxygen]

As the oxygen, any of molecular oxygen and nascent oxygen can be used. Such molecular oxygen includes, but is not limited to, pure oxygen, and oxygen diluted with an inert gas such as nitrogen, helium, argon or carbon dioxide. Air is preferably used as the molecular oxygen from the viewpoints of operating property and safety, as well as cost efficiency.

The proportion of the oxygen can be appropriately selected depending on the type of the substrate, and generally is, for example, 0.5 mole or more (e.g., 1 mole or more), preferably about 1 to 100 moles, and more preferably about 2 to 50 moles, per 1 mole of the substrate. The oxygen is often used in excess moles with respect to the substrate.

[Reaction]

The reaction can be performed either in a liquid phase or in agaseous phase. In a liquid phase reaction, the reaction is generally performed in an organic solvent. Such organic solvents include, but are not limited to, benzene, toluene, xylene, ethylbenzene, trifluoromethylbenzene (trifluorotoluene), chlorobenzene, anisole, benzonitrile, nitrobenzene, ethyl benzoate, and other benzene derivatives whose benzene ring may be substituted with, for example, a halogen atom, an alkyl group, a haloalkyl group, an alkoxy group, a cyano group, a nitro group, or a substituted oxycarbonyl group; hexane, heptane, octane, and other aliphatic hydrocarbons; cyclohexane, and other alicyclic hydrocarbons; carbon tetrachloride, chloroform, dichloromethane, 1,2-dichloroethane, and other haloalkanes; acetone, methyl ethyl ketone, and other ketones; methyl acetate, ethyl acetate, isopropyl acetate, butyl acetate, and other esters; N,N-dimethylformamide, N,N-dimethylacetamide, and other amides; acetonitrile, propionitrile, and other nitrites; diethyl ether, dibutyl ether, dimethoxyethane, dioxane, tetrahydrofuran, and other chain or cyclic ethers; and acetic acid, and other organic acids. Preferred solvents are benzene, toluene, trifluoromethylbenzene, and other benzene derivatives mentioned above, 1,2-dichloroethane, and other haloalkanes, and ethyl acetate, and other esters, of which trifluoromethylbenzene and other benzene derivatives whose benzene ring is substituted with a haloalkyl group are specifically preferred. Each of these solvents can be used alone or in combination.

A reaction temperature can be appropriately selected depending on, for example, the type of the 1,2-diol, and is for example about 0° C. to 200° C., preferably about 10° C. to 150° C., and more preferably about 30° C. to 120° C. The reaction can be carried out at atmospheric pressure or under a pressure (e.g., 1 to 100 atm). The reaction can be performed in a batch system, a semi-batch system, a continues system or any other systems.

According to the invented process, a bond between two carbon atoms in the 1,2-diol, where hydroxyl groups are combined with the carbon atoms, is oxidatively cleaved as a result of reaction even under mild conditions, to thereby yield a corresponding aldehyde. For example, when a 1,2-diol represented by the formula (1) is subjected to the reaction, an aldehyde represented by the following formula (2) and/or the formula (3) is formed:

$$R^a CHO \qquad (2)$$

$$R^b CHO \qquad (3)$$

(wherein $R^a$ and $R^b$ have the same meanings as defined above). When $R^a$ and $R^b$ in the compound represented by the formula (1) are combined to form a ring with adjacent two carbon atoms, a bond between the two carbon atoms is oxidatively cleaved as a result of reaction to thereby yield a corresponding dialdehyde having two formyl groups at terminals.

After the completion of the reaction, reaction products can be easily separated and purified by a conventional technique such as filtration, concentration, distillation, extraction, crystallization, recrystallization, column chromatography, and other separation means, and combinations of these separation means.

The invented process uses a specific catalyst and can therefore allow a 1,2-diol to oxidatively cleave with oxygen to thereby efficiently yield a corresponding aldehyde.

The present invention will now be illustrated in further detail with reference to several examples below, which are not intended to limit the scope of the invention.

EXAMPLE 1

A mixture of 0.1 mmol (in terms of ruthenium compound) of a 4% by weight $Ru(PPh_3)_3Cl_2$ [dichlorotris(triphenylphosphine) ruthenium(II)]/C, 5 mmol of 1,2-octanediol, and 25 ml of trifluoromethylbenzene was stirred at 60° C. in an oxygen atmosphere (1 atm) for 15 hours. Products were separated by column chromatography on a silica gel to yield heptanal in a yield of 71%. In this connection, 4-heptyl-2-hexyldioxolane was formed in a yield of 9%, but no corresponding carboxylic acid was formed.

COMPARATIVE EXAMPLE 1

The procedure of Example 1 was repeated, except that 0.1 mmol of $Ru(PPh_3)_3Cl_2$ which was not supported on a carrier was used instead of the 4% by weight $Ru(PPh_3)_3Cl_2/C$ to thereby yield heptanal in a yield of 13%.

EXAMPLE 2

A mixture of 0.1 mmol (in terms of ruthenium compound) of a 4% by weight $Ru(PPh_3)_3Cl_2/C$, 5 mmol of 1-phenyl-1,2-ethanediol, and 25 ml of trifluoromethylbenzene was stirred at 60° C. in an oxygen atmosphere (1 atm) for 15 hours. Products were separated by column chromatography on a silica gel to thereby yield benzaldehyde in a yield of 85%.

EXAMPLE 3

A mixture of 0.1 mmol (in terms of ruthenium compound) of a 4% by weight $Ru(PPh_3)_3Cl_2/C$, 5 mmol of 2,3-octanediol, and 25 ml of trifluoromethylbenzene was stirred at 60° C. in an oxygen atmosphere (1 atm) for 15 hours. Products were separated by column chromatography on a silica gel to thereby yield hexanal in a yield of 61%.

EXAMPLE 4

A mixture of 0.1 mmol (in terms of ruthenium compound) of a 4% by weight $Ru(PPh_3)_3Cl_2/C$, 0.15 mmol of potassium carbonate, 5 mmol of trans-1,2-cyclooctanediol, and 25 ml of trifluoromethylbenzene was stirred at 60° C. in an oxygen atmosphere (1 atm) for 15 hours. Products were separated by column chromatography on a silica gel to thereby yield octanedial in a yield of 62%.

What is claimed is:

1. A process for producing an aldehyde comprising the step of allowing a 1,2-diol to react with oxygen in the presence of an organic ruthenium complex as a catalytic component supported on a carrier to oxidatively cleave a bond between two carbon atoms, hydroxyl groups being combined with said carbon atoms, to thereby yield a corresponding aldehyde.

2. The process for producing an aldehyde according to claim 1, wherein said carrier is an activated carbon.

3. The process for producing an aldehyde according to claim 1 or 2, wherein the organic ruthenium complex is dichlorotris(triphenylphosphine)ruthenium (II).

* * * * *